United States Patent

Mälkki et al.

Patent Number: 5,929,231
Date of Patent: Jul. 27, 1999

[54] METHOD FOR PREPARING FINE-GRANULED AND MODIFIED STARCHES

[75] Inventors: Yrjö Mälkki; Olavi Myllymäki; Risto Tuomela, all of Espoo, Finland

[73] Assignee: Exavena Oy, Espoo, Finland

[21] Appl. No.: 08/750,133

[22] PCT Filed: May 30, 1995

[86] PCT No.: PCT/FI95/00302

§ 371 Date: Jan. 17, 1997

§ 102(e) Date: Jan. 17, 1997

[87] PCT Pub. No.: WO95/32993

PCT Pub. Date: Dec. 7, 1995

[30] Foreign Application Priority Data

May 31, 1994 [FI] Finland .................................. 942546

[51] Int. Cl.⁶ .............................. C08B 30/04; C12P 19/04
[52] U.S. Cl. ................... 536/127; 435/101; 435/274; 435/275; 127/71; 127/65
[58] Field of Search ..................... 435/101, 275, 435/274; 127/65, 71; 536/127

[56] References Cited

U.S. PATENT DOCUMENTS

| 3,368,903 | 2/1968 | Johnson et al. ........................... 426/20 |
| 3,488,256 | 1/1970 | High et al. ............................... 435/275 |
| 3,537,893 | 11/1970 | Hauser et al. . |
| 4,916,064 | 4/1990 | Derez et al. .............................. 435/99 |

FOREIGN PATENT DOCUMENTS 0 378 522  7/1990  European Pat. Off. .
0 381 872  9/1995  European Pat. Off. .

OTHER PUBLICATIONS

Juliano, "Rice Starch: . . . ," Chapter XVI of *Starch: Chemistry and Technology*, 2nd ed, Whistler et al eds., 1984, pp. 507–528.

STN International, File FSTA, Fsta accession No. 86(09):L0077, Gough, B.M. et al. "On the interaction of sodium dodecyl sulphate with starch granules", (1985) pp. 99–108. (Abstract only).

*Primary Examiner*—Francisco Prats
*Attorney, Agent, or Firm*—Pennie & Edmonds LLP

[57] ABSTRACT

The subject of the invention is a method for preparing fine-granuled starch from kernels of oats or rice. In the method, the kernels are ground and the starch is separated from the starch containing fraction obtained by the milling. An essential feature of the invention is that a suspension of the said fraction or of starch separated from it is treated with a surface-active agent or a lipolytic enzyme for disintegrating compound granules or aggregates of starch granules. Except the particle size, also functional properties of starch are affected. Disintegration of compound granules is enhanced by alkaline conditions and by mixing of the suspension. The fine-granuled starch obtained can be applied in foods and, for instance, for biodegradable plastics and for surface treatment agents. The invention can be included as a part of an integrated fractionation process, in which, in addition to starch, an oil fraction, an enriched fibre fraction, and a surplus fraction suitable for feed, are obtained.

11 Claims, 1 Drawing Sheet

METHOD FOR PREPARING FINE-GRANULED AND MODIFIED STARCHES

This application is a 371 of international application number PCT/FI95/00302, filed May 30, 1995.

TECHNICAL FIELD

The subject of this invention is separation and purification of fine-granuled and modified starches from oat or rice groats.

Cereal crops used for manufacturing of starch have been so far mainly corn and wheat. As compared to these crops, use of rice for starch manufacture is less common. When used, the raw material consists usually for economical reasons of mechanically or enzymatically damaged kernels of rice. Despite the properties of rice starch deviate from other cereal starches, its industrial use has remained smaller as compared to other cereal starches. This is partly due to its higher price, partly due to fluctuations in quality deriving of the problems in the quality of raw material said above. Barley and rye have been used in the manufacture of starch mainly for finding demand for surplus crops. These starches have no such special properties that would give them an advantage over other cereal starches.

Unlike most other cereal starches, oat starch has a small granule size. The primary granules are usually 3 to 5 μm in dimensions and the shape is globular or angular. In the kernels of oats and rice, the starch is for its main part in compound granules. In the endosperm of rice, the starch is totally in compound granules, whereas in oats also individual granules occur. The small granule size makes it possible to use oat starch technologically for several purposes for which rice starch has been used so far. Also the gelatinization properties of native oat starch deviate from other cereal starches, due at least partly to the amount and composition of lipids in the starch granules.

BACKGROUND OF THE INVENTION

Recovery of oat starch has been earlier presented mainly as a by-product in the preparation of protein or fibre concentrates. In most of these methods, separation is not presented further than until oat flour, or for the removal of starch for enriching the main products. Thus the U.S. Pat. No. 4,028,468 describes a process, where oat gum, starch and protein are separated from the bran by wet milling in sodium carbonate solution. Starch is separated by an effective centrifugation of the viscous solution, but any further separation of starch nor the purity of the recovered starch is given. The granule size of starch is said to be 5 to 10 μm. Similarly, the Canadian Patent 1,133,446 describes separation of the endosperm from milled oats, but purification of starch only for testing purposes using laboratory methods. U.S. Pat. No. 4,211,801 describes separation in an organic solvent, whereby of oat flour free of oat gum is prepared, but separation of starch from it is not described.

Separation and purification of starch are described in detail in the European Patent Application 89.200321.1, and in the corresponding Finnish application 900508. The method is based on wet milling in a solution containing sulfur dioxide, and subsequent sieving and hydrocyclone operations. For achieving the separation of starch from cell walls, enzymes degrading cell wall components such as cellulose, hemicellulose and β-glucan are used. The particle size distribution of the starch obtained using this method is according to the patent specification within limits 4–15 μm.

Enzymatic steps are also included in processes where starch is further hydrolysed to maltodextrin, as in the U.S. Pat. Nos. 4,996,063 and 5,082,673. These methods are, however, not intended for separation of unhydrolyzed starch. In a method according to the Canadian Patent 1,179,189, hull-less oat groats are soaked in sulfur dioxide containing water for 24–28 hours at 50° C. The inherent enzymatic activity of the kernel decomposes cell wall material, and the endosperm containing starch is separated from the bran by squeezing. In this method, too, no description of starch separation is included.

In the method described in the Finnish Patent 84,775 and in the corresponding European Patent 379,499, oat endosperm is treated in sodium hydroxide solution to decrease the protein content. The patent specification does not give information on the particle size distribution.

DETAILED DESCRIPTION OF THE INVENTION

Figure 1:
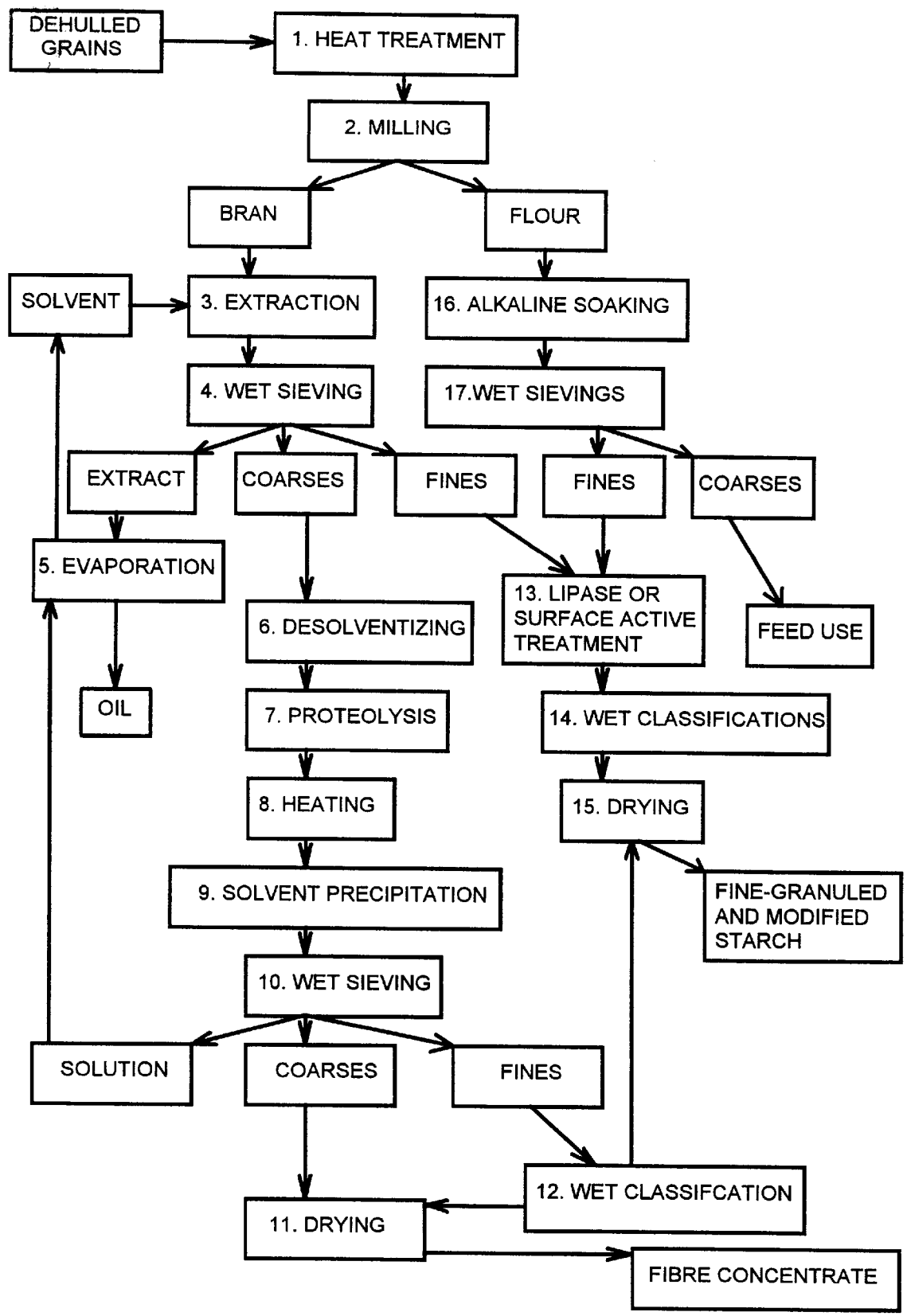
FIG. 1 is a flow diagram of an integrated process for fractionation and treatment of oats according to the present invention.

The nature of bonds in the compound starch granules of oats or rice and the separation of individual granules from them are not closely described in the scientific literature nor in patents. In the ordinary processes including a treatment in alkaline suspensions, mechanical homogenization, and dry milling, individual granules are only difficultly separated of compound granules. Even after being separated they remain in aggregates consisting of 2 to 10 individual granules. One compound granule can contain tens of individual granules, and in electron micrographs the compound granule has often a ball shape. Correspondingly, compound granules that are difficultly decomposed occur also in rice starch.

In technological applications where a small granule size is important, it is also important that the granule size distribution is as homogeneous as possible. Examples of such cases are mixing of starch into plastics for preparing biodegradable materials, or in release or surface treatment agents. When classifications are used for achieving fine-granuled and homogeneous starches, great losses of material can occur, unless compound granules and aggregates have been effectively decomposed in the process.

The principal factors affecting functional properties of starches are the ratio of amylose and amylopectin, mechanical damages of the granule, leaching of starch molecules outside the granules, and complexing of starch by lipids. The lipid content of oat starch is inherently higher than that of other cereal starches. This evidently affects, among others, temperature of gelatinization, the amount of starch outside the granules, and freezing-thawing stability. A remarkable part of the lipids of starches is inside the granules. Therefore, treatments with lipid solvents at low temperatures remove only a part of the lipids, and the effect on functional properties remains small. Extractions in butanol-water mixtures at their boiling temperatures for several hours can remove bound lipids and alter functional properties of the starches. A treatment at high temperatures in the presence of water leads, however, easily to leaching of starch outside the granule, to disintegration of the granule, and to gelatinization of starch.

In the background research for this invention it has now been surprisingly observed, that compound granules and aggregates consisting of several individual granules can be disintegrated by surface active compounds or lipolytic enzymes. This can occur when they are added to suspensions of oat flour or of partly or completely purified starch. Both anion active, cation active and non ionic surface active compounds can have this effect. The disintegration is enhanced by a simultaneous mixing and by alkaline conditions. It was also noticed, that extracting fats enhances the disintegration of compound granules and aggregates by means of surface-active compounds. The effect is most probably due partly to dispersing or dissolving of compounds binding the particles together, partly to the decrease of interfacial tension and its effect in enhancing water penetration and swelling.

Essential characteristics of this invention are presented in the Claims attached.

When preparing starches for non food purposes, addition of synthetic anion active compounds such as alkyl sulfates or alkyl aryl sulfonates can be used. In preparing starches for food and pharmaceutical purposes, alkali salts of fatty acids or food and pharmaceutical grade non ionic or weakly ionized surface active agents such as those marketed under trade name Tween can be added. Alternatively, the lipids in the starch can be hydrolysed using microbial lipases or extracts of plant or animal products containing lipolytic activity, or by adding enzymes isolated from these. Also an addition of cationic surface active compounds such as cetyl pyridinium chloride leads to disintegration of compound granules and aggregates, and simultaneously a microbicidic effect is achieved. Enzymes and conditions of use have to be selected in such a way, that no remarkable hydrolysis of starch can occur. Other steps in the preparation of starch can be performed by using unit operations and techniques known as such. However, requirements of the product, the fine-granuled and slowly sedimenting starch, have to be considered in the choice of equipment and process parameters.

The treatments presented above affect not only the disintegration of compound granules and aggregates, but also the functional properties of the starch. Without committing to any mechanism of action it seems possible, that the surface active compounds remove a part of lipids bound in the starch and complexing it. Lipolytic enzymes hydrolyse lipids bound to or adsorbed on the starch thus altering their starch complexing effect. Each of these phenomena can affect the amount of starch outside the granules, and in water absorption, water binding, gelatinization and viscosity properties and the hydrolysability by enzymes.

The invention can be advantageously integrated to processes where cereal materials are fractionated and starch is separated from other components. The conditions and the active ingredients can then be chosen in such a way, that means described in this invention are applied. Operation steps according to this invention can be included in the total process, and objectives of this invention are thus simultaneously achieved. As an example, processing steps now described can be combined in fractionations and treatments which are performed according to the Finnish Patent 84,775 and the Finnish Patent Application 932,558. FIG. 1 attached presents such an integrated process for fractionating oats and further treatment of the fractions. Stages 1 to 6 and 16 to 17 of the figure can then be performed following the methods presented in the Finnish Patent 84,775, stages 7 to 12 according to the Finnish Patent Application 932,558, and stages 13 to 15 according to the method now presented. The extraction performed as stage 3 removes the main part of fat, which is of advantage for performing the method now described. In the proteolysis at the stage 7, enzymes can be applied, which besides proteases also contain lipase activity, and can thus affect the starch fraction according to the method now described.

EXAMPLES

Application of the invention is described in the following examples. As raw material in the examples, oat or fractions separated from it have been used, but the same methods can be applied also for rice or rice starches.

EXAMPLE 1

Dehulled oats were milled using a roller mill with uncorrugated rolls, and bran was separated by sieving. 5 kg of the flour obtained was suspended in 100 liters of water, pH of the mixture was adjusted to the value 9.0 with sodium hydroxide, and the mixture was allowed to stand overnight at room temperature. Coarse components were separated from the suspension by sieving it with a vibrating screen having openings of 125 $\mu$m, performing four subsequent sievings. To the mixture passing the sieves, 100 ml of a 25% solution of sodium dodecyl sulfate was added, and the mixture was blended with a blade mixer overnight at room temperature. Fibre separated was removed by wet sieving using sieves with openings of 75 $\mu$m. Starch was further purified by separating larger particles in a hydrocyclone having a diameter of 10 mm, separated from the water by centrifugation, and air dried. In the product obtained, before further classifications, the individual granules made 95% of the particles. Light absorption coefficient of the dry starch obtained, as measured from a layer thickness of 8.4 g/m$^2$, was 0.97 m$^2$/g, whereas that of the native oat starch, as measured from a layer thickness of 7.5 g/m$^2$, was 0.186 m$^2$/g, and from a layer thickness of 8.9 g/m$^2$ it was 0.162 m$^2$/g.

EXAMPLE 2

Five lots, 2 g each, of a starch sieved from oat meal suspended in sodium hydroxide solution, were suspended each in 100 ml of water, and the following additions were made:

(a) 0.2 g of sodium dodecyl sulfate
(b) 0.2 g of alkyl benzene sulfonate
(c) 0.2 g of Tween 20
(d) 0.2 g of cetyl pyridinium chloride
(e) no additions.

The lots were stirred with magnetic stirrers overnight at about 30° C., after which each lot was subjected to microscopical observation. In lots a, b and c starch was nearly totally disintegrated to individual granules. No clear difference in the effect of these three surface active compounds could be observed. In lot e, the change from the particle size distribution before the test was slight.

EXAMPLE 3

15 g of oat flour, obtained from wet sieving of oat bran after being extracted during 2 hours at 75° C. with ethanol and subsequent drying, was suspended in 150 ml of distilled water, and 300 mg of lipase produced by *Candida cylindrica* (Biocatalysts, England) was added to the mixture. This enzyme is an unspecific lipase, which also hydrolyses phospholipids. The mixture was stirred overnight with a magnetic stirrer at ca. 30° C., and the coarse part was separated by sieving the suspension with a 60 $\mu$m sieve. Starch was separated by centrifuging and subjected to microscopy. In the unfractionated starch obtained, the majority of the particles consisted of individual starch granules. In addition about 10% of the mass was in aggregates of 2 to 10 individual granules. A similar result was obtained by using lipase produced by *Penicillium cyclopium* (Biocatalysts), which is 1,3 specific towards fats, but hydrolyses from phospholipids fatty acids from both positions. The treatment was made in a buffer solution of pH 4.5, in the presence of calcium.

EXAMPLE 4

Effect of the treatments to functional properties of the starches was studied by differential scanning calorimetry from the following samples:
- (a) starch separated from an alkaline solution according to Example 1, but without a treatment with surface active substances
- (b) starch prepared according to Example 3 from ethanol extracted flour, but without any enzymatic treatment
- (c) starch prepared according to Example 3, treated with lipase of *Candida cylindrica*
- (d) starch prepared according to Example 3, treated with lipase of *Penicillium cyclopium*

TABLE

Effect of solvent and enzyme treatments on calorimetric properties of starches. $\Delta H_{gel}$ = gelatinization enthalpy, $T_p$ = maximum temperature of the gelatinization endotherm, $\Delta H_{AML}$ = dissociation enthalpy of amylose-lipid complex, $T_p^{AML}$ = its maximum temperature.

| Treatment | $\Delta H_{gel}$, J/g | $T_p$, °C. | $\Delta H_{AML}$, J/g | $T_p^{AML}$, °C. |
|---|---|---|---|---|
| a) alkaline separation | 9.4 | 63.2 | 0.8 | 98.9 |
| b) ethanol extraction | 6.3 | 62.3 | 0.5 + 0.5 | 100 + 112 |
| c) ethanol extraction, lipase of *C. cylindrica* | 9.3 | 62.4 | 2.4 | 99.9 |
| d) ethanol extraction, lipase of *P. cyclopium* | 8.8 | 62.5 | 2.5 | 101 |

According to the Table, treatments with lipases cause changes in the amylose-lipid complex, which reflects in changes in the functional properties.

We claim:

1. A method for preparing individual granules of starch from kernels of oat or rice, which consists essentially of:
    milling the kernels to produce a starch having compound granules or aggregates of granules;
    separating the starch from the milled kernels;
    suspending the separated starch in an aqueous solution; and
    contacting the suspended starch with an amount of a surface active compound sufficient to disintegrate at least a portion of the starch compound granules or aggregate granules into individual granules of non-hydrolyzed starch, wherein the amount of surface active compound is about 0.02 to about 0.2% by weight, based on the weight of the aqueous solution.

2. The method according to claim 1, wherein the surface active compound is anionic.

3. The method according to claim 2, wherein the surface active agent compound is sodium dodecyl sulfate or an alkyl benzene sulfonate.

4. The method according to claim 2, wherein the surface active compound is an alkali metal salt of a fatty acid.

5. The method according to claim 1, wherein the surface active compound is non-ionic.

6. The method according to claim 1, wherein the surface active compound is cationic.

7. The method according to claim 1, which further comprises extracting fat from the starch with an organic solvent to remove a portion of the fat before contacting the starch with the surface active compound.

8. The method according to claim 1, wherein the individual granules have an average diameter of 3 to 5 µm.

9. The method according to claim 1, wherein the surface active compound is selected from the group consisting of sodium dodecyl sulfate, alkyl benzene sulfonate, an alkali metal salt of a fatty acid, and mixtures thereof.

10. A method for preparing individual granules of starch from kernels of oat or rice, which consists essentially of:
    milling the kernels to produce a starch having compound granules or aggregates of granules;
    separating the starch from the milled kernels;
    suspending the separated starch in an aqueous solution;
    subjecting the starch to alkaline soaking; and
    contacting the suspended starch with an amount of a surface active compound sufficient to disintegrate at least a portion of the starch compound granules or aggregate granules into individual granules of non-hydrolyzed starch, wherein the amount of surface active compound is about 0.02 to about 0.2% by weight, based on the weight of the aqueous solution.

11. A method for preparing individual granules of starch from kernels of oat or rice, which consists essentially of:
    milling the kernels to produce a starch having compound granules or aggregates of granules;
    separating the starch from the milled kernels;
    suspending the separated starch in an aqueous solution;
    subjecting the starch to fat removal by solvent extraction; and
    contacting the suspended starch with an amount of a surface active compound sufficient to disintegrate at least a portion of the starch compound granules or aggregate granules into individual granules of non-hydrolyzed starch, wherein the amount of surface active compound is about 0.02 to about 0.2% by weight, based on the weight of the aqueous solution.

* * * * *